US006875792B2

(12) United States Patent
Brusilow et al.

(10) Patent No.: US 6,875,792 B2
(45) Date of Patent: Apr. 5, 2005

(54) DOSAGE FORM OF L-METHIONINE S-SULFOXIMINE

(75) Inventors: Saul Brusilow, Baltimore, MD (US); Richard J. Traystman, Ruxton, MD (US); Raymond C. Koehler, Baltimore, MD (US)

(73) Assignee: MSO Pharma LLC, Chevy Chase, MD (US)

( * ) Notice: Subject to any disclaimer, the term of this patent is extended or adjusted under 35 U.S.C. 154(b) by 0 days.

(21) Appl. No.: 10/060,099

(22) Filed: Jan. 31, 2002

(65) Prior Publication Data

US 2003/0144357 A1 Jul. 31, 2003

(51) Int. Cl.[7] .............................................. A61K 31/198
(52) U.S. Cl. ....................................................... 514/562
(58) Field of Search .......................................... 514/562

(56) References Cited

PUBLICATIONS

Takahashi et al., Circulation Research, 71(5), 1220–1230 (Nov., 1992).*

Harth et al., J. Exp. Med., 189(9), 1425–1435 (May 3, 1999).*

Apostolakis et al., Brain Research Bulletin, vol. 23, pp. 257–262 (1989).*

Ginefri–Gayet et al., Pharmacology Biochemistry and Behavior, vol. 43, pp. 173–179 (1992).*

Blei, Andres T., et al., "Ammonia–Induced Brain Edema and Intracranial Hypertension in Rats After Portacaval Anastomosis," *Hepatology* 19(6): 1437–1444, Jun. 1994.

Brusilow, Saul W. "Inborn Errors of Urea Synthesis," *In: Scriver CR, Lloyd Jk, eds. Genetic and Metabolic Disease in Pediatrics*. 5: 140–165, London: Butterworths, 1985.

Brusilow, Saul W., et al., "Urea Cycle Disorders: Diagnosis, Pathophysiology, and Therapy," *Advances in Pediatrics* 43:127–170, 1996.

Butterworth, R.F., "Effects of Hyperammonaemia on Brain Function," *J. Inher. Metab. Dis.* 21(1):6–20, 1998.

Cordoba, Juan, et al., "Brain Edema and Hepatic Encephalopathy," *Seminars in Liver Disease* 16(3): 271–280, 1996.

Folbergrova, J., "Free Glutamine Level in the Rat Brain In Vivo After Methionine Sulphoximine Administration," *Physiologia Bohemoslovenica* 13:21–26, 1963.

Gershoff, S.N., et al., "The Relative Effect of Methionine Sulfoximine on Different Animal Species," *J. Nutr.* 45:451–458, 1951.

Häussinger, Dieter, et al., "Pathogenesis of Hepatic Encephalopathy," *Journal of Gastroenterology and Hepatology* 17:S256–S259, 2002.

Hawkins, Richard, et al., "Effect of Reducing Brain Glutamine Synthesis on Metabolic Symptoms of Hepatic Encephalopathy," *Journal of Neurochemistry* 60(3):1000–1006, 1993.

Hawkins, Richard, et al., "Hyperammonaemia Does Not Impair Brain Function in the Absence of Net Glutamine Synthesis," *Biochem. J.* 277:697–703, 1991.

Hirata, Takahiko, et al., "Impaired Pial Arteriolar Reactivity to Hypercapnia During Hyperammonemia Depends on Glutamine Synthesis," *Stroke* 27(4): 729–736, 1996.

Jonung, Torbjorn, et al., "Methionine Sulfoximine Prevents the Accumulation of Large Neutral Amino Acids in Brain of Hyperammonemic Rats," *J. Surgical Research* 36:349–353, 1984.

Krakoff, Irwin H., et al., "Effect of Methionine Sulfoximine in Man," *J. Pharm. Experimenetal Ther*. 2:599–604, 1961.

Lamar, C., et al., "The Duration of the Inhibition of Glutamine Synthetase by Methionine Sulfoximine," *Biochemical Pharmacology* 17:636–640, 1968.

Master, Sonali, et al., "Cerebral Blood Flow and the Development of Ammonia–Induced Brain Edema in Rats After Portacaval Anastomosis," *Hepatology* 30(4): 876–880, 1999.

Norenberg, Michael D., et al.,"Fine Structural Localization of Glutamine Synthetase in Astrocytes of Rat Brain," *Brain Research* 161:303–310, 1979.

Richman, Paul G., et al., "Inhibition of y–Glutamylcystein Synthetase by L–Methionine–S–Sulfoximine," *J. Biological Chemistry* 248(19): 6684–6690, 1973.

Rowe, W. Bruce, et al., "Identification of L–Methionine–S–Sulfoximine as the Convulsant Isomer of Methionine Sulfoximine," *Proceedings of the National Academy of Sciences* 66(2): 500–506, Jun. 1970.

Sellinger, Otto Z., et al., "Methionine Sulfoximine Seizures. VII. the Dissociation of the Convulsant and Glutamine Synthetase Inhibitory Effects," *J. Pharmacology & Experimental Therapeutics* 161(1): 212–222, 1968.

Sugimoto, Hideyoshi, et al., "Methionine Sulfoximine, A Glutamine Synthetase Inhibitor, Attenuates Increased Extracellular Potassium Activity During Acute Hyperammonemia," *Journal of Cerebral Blood Flow & Metabolism*, 17:44–49, 1997.

Takahashi, Hideo, et al., "Inhibition of Brain Glutamine Accumulation Prevents Cerebral Edema in Hyperammonemic Rats," *American Physiological Society* 261:H825–H829, 1991.

(Continued)

*Primary Examiner*—Phyllis G. Spivack
(74) *Attorney, Agent, or Firm*—Rothwell Figg Ernst & Manbeck p.c.

(57) ABSTRACT

Methods for the treatment of both diseases susceptible to the inhibition of mammalian glutamine synthetase and progressive hyperammonemic encephalopathy comprising administering L-methionine S-sulfoxime at a dose not to exceed 10 mg/kg body weight are disclosed. Preferably, the dose should not exceed 8 mg/kg; more preferably, the dose should not exceed 5 mg/kg; most preferably, the dose should not exceed 2.5 mg/kg.

33 Claims, 1 Drawing Sheet

PUBLICATIONS

Voorhies, Theresa M., "Acute Hyperammonemia in the Young Primate: Physiologic and Neuropathologic Correlates," *Pediatric Research* 17(12):970–975, 1983.

Wada, Juhn A., et al., "The Susceptibilty of Auditory Stimuli of Animals Treated with Methionine Sulfoximine," *Experimental Neurology* 15:157–165, 1966.

Warren, Kenneth S., et al., "Effect of an Inhibitor of Glutamine Synthesis (Methionine Sulfoximine) on Ammonia Toxicity and Metabolism," *J. Lab. & Clin. Med.* 64(3): 442–449, 1964.

Watson, Alan J., et al. "Transient Idiopathic Hyperammonaemia in Adults," *The Lancet* 1271–1274, Dec. 7, 1985.

Willard–Mack, C.L., et al., "Inhibition of Glutamine Synthetase Reduces Ammonia–Induced Astrocyte Swelling in Rat," *Neuroscience* 71(2): 589–599, 1996.

Zwingmann, Claudia, et al., Multinuclear NMR Spectroscopy Studies on NH4CI–Induced 7Metabolic Alterations and Detoxification Processes in Primary Astrocytes and Glioma Cells, *Dev. Neurosci* 20:417–426, 1998.

* cited by examiner

DOSAGE FORM OF L-METHIONINE S-SULFOXIMINE

BACKGROUND OF THE INVENTION

The Gersoff reference entitled "The Relative Effect of Methionine Sulfoximine on Different Animal Species" reported the results of experiments involving the intraperitoneally injected methionine sulfoximine (hereinafter "MSO") into rats, the subcutaneous injection of MSO into mongrel puppies, and intraperitoneal injections of MSO into monkeys. The experiments determined the minimum toxic doses of MSO for dogs, rats and monkeys. It was further determined that rats and monkeys are approximately 100 times more resistant to MSO than dogs. It was also discovered that MSO-induced seizures could be suppressed by the administration of methionine. The amount ratio for methionine (which prevents seizures) to MSO (which causes seizures) was determined in monkeys and dogs. As stated above, Gershoff demonstrates species specificity for toxicity and also that dogs are especially vulnerable whereas monkeys (primates are not). It was also shown that monkeys could withstand doses of 50 and 100 mg/kg of mixed isomers of MSO. Gershoff, "The Relative Effect of Methionine Sulfoximine on Different Animal Species," J Nutr 45:451–458 (1951).

The Krakoff reference entitled "Effect of Methionine Sulfoximine in Man" involved the administration of MSO to hospitalized patients with far-advanced, nonresectable cancer. The MSO was given in divided doses every 6 or 8 hours. The result of this experiment was no change in hepatic or renal function or in hematological status. Further, no evidence of tumor regression was discovered. It was noted that MSO impacted the central nervous system in the form of hallucinations, disorientation, and marked agitation. The author suggested that the symptoms were related to the size of the daily dose rather than a cumulative dose. In the reported experimentation, each patient was given a laboratory evaluation of their hepatic, renal, and hematologic status before the experimentation began. These evaluations were continued at regular intervals during the course of the experimentation and each subject was watched for evidence of tumor regression, measurable either enterogenographically or by direct observation of tumor masses. No evidence of tumor regression was noted.

It was also noted that the abnormal mental state cleared on its own and without the addition of methionine. The reference also disclosed that the most probable reason that convulsions did not occur in the test subjects was that the MSO had been withdrawn before the convulsive state had been reached. It was stated that the precise mechanism by which the methionine analogues produce their toxic effects was not known, but the article disclosed that MSO appears to inhibit the incorporation of other amino acids into protein, and that this inhibition is prevented by glutamine. The article continued to disclose that the synthesis of glutamine from glutamate and the transfer of glutamyl groups have been inhibited by MSO. However, the article could not disclose whether MSO's relationship to glutamine is responsible for the neurotoxicity of MSO or for its potentiation of the tumor-inhibitory effects of the glutamine antagonists azaserine and DON. Lastly, it noted that the effects of MSO and ethionine in man are not identical. Krakoff, Effect of Methionine Sulfoximine in Man," *J. Pharm. Experimental Ther.*, 2:599–604 (1961).

The Folbergrova reference entitled "Free Glutamine Level in the Rat Brain In Vivo After Methionine Sulphoximine Administration" studied whether the inhibition of free glutamine synthesis in the brain might be associated with the neurotoxic action of MSI (this article's abbreviation for MSO) and the onset of seizures. It was disclosed that the administration of MSI lead to a state which may be characterized as epileptic. The mechanism that triggers this state, however, remained unknown. It was disclosed that MSI inhibited the synthesis of free glutamine in the brain tissue and that the brain tissue of animals in MSI seizures contained significantly reduced levels of glutamine. It was noted that when MSI was injected in a dose of 100 mg/kg and 50 mg/kg, both doses being subthreshold, rats exhibited no paroxysmal symptoms for 20 hours and did not differ in any way from the control animals. It was further noted that 20 hours after the administration of the MSI that the levels of glutamine were reduced to the same degree as in rat brains with the paroxysmal dose. The article concluded that based upon the results of using paroxysmal doses, it appeared that the onset of seizures could be associated with impaired glutamine synthesis. Folbergrova, "Free Glutamine Level in the Rat Brain In Vivo After Methionine Sulphoximine Administration," *Physiologia Bohemoslovenica* 13:21–26 (1963).

The Warren reference entitled "Effect of an Inhibitor of Glutamine Synthesis (Methionine Sulfoximine) on Ammonia Toxicity and Metabolism" disclosed that glutamine formation is the major pathway of ammonia detoxification in tissues other than the liver and that when MSO was administered to mice, there was a marked decrease in in vivo ammonia toxicity. MSO also was shown to have an effect on endogenous ammonia metabolism, as demonstrated by the doubling of the brain ammonia concentrations 2 hours after its administration. The increase was sustained for 24 hours. It was discovered, against expectations, that MSO protected mice from ammonia toxicity. Warren, "Effect of an Inhibitor of Glutamine Synthesis (Methionine Sulfoximine) on Ammonia Toxicity and Metabolism," *J. Lab. & Clin. Med.* 64:3, 442449 (1964).

The Wada reference entitled "The Susceptibility to Auditory Stimuli of Animals Treated with Methionine Sulfoximine" disclosed that cats and rats treated with MSO and subjected to repeated sounds responded to the sounds with episodic running behavior and that the most effective dosage of MSO was 7.5 mg/kg. It was also disclosed that these effects were completely reversible. It was noted that amounts less than 5 mg/kg did not render cats susceptible whereas 10 mg/kg tended to produce early convulsive episodes that often ended in status epilepticus. Wada, "The Susceptibility to Auditory Stimuli of Animals Treated with Methionine Sulfoximine," *Experimental Neurology* 15: 157–163 (1966).

The Lamar reference entitled "The Duration of the Inhibition of Glutamine Synthetase by Methionine Sulfoximine" disclosed the duration of inhibition of glutamine synthetase and glutamine transferase activities in liver, brain and kidney cells after a single injection of MSO. Lamar disclosed that the maximal inhibition in the brain was 24 hours, but that the inhibition remains to a considerable degree for 72 hours, and that at the end of one week, the activity had not returned to normal levels. Lamar, "The Duration of the Inhibition of Glutamine Synthetase by Methionine Sulfoximine," *Biochemical Pharmacology* 17: 636–642 (1968).

The Rowe reference "Identification of L-Methionine-S-Sulfoximine as the Convulsant Isomer of Methionine Sulfoximine" disclosed that MSO inhibits brain glutamine synthesis irreversibly and the inhibitor becomes bound to the active site of the enzyme as methionine sulfoximine phosphate. L-methionine-S-sulfoximine also was disclosed as inhibiting glutamine synthetase and inducing convulsions. It was concluded that ammonia and MSO seem to produce seizures by different mechanisms affecting different regions of the brain. Rowe, "Identification of L-Methionine-S-Sulfoximine as the Convulsant Isomer of Methionine Sulfoximine," *Proceedings of the National Academy of Sciences* 66:2, 500–506 (1970).

The Richman reference entitled "Inhibition of γ-Glutamylcysteine Synthetase by L-Methionine-S-Sulfoximine" disclosed that MSO was an effective inhibitor of γ-glutamylcysteine synthetase. MSO is disclosed as binding to the glutamate site of the enzyme and is converted into methionine sulfoximine phosphate in the presence of ATP and either $MG^{2+}$ or $Mn^{2+}$ ions. It was taught in this reference as well that only L-methionine-S-sulfoximine inhibits the enzyme and causes convulsions in mice. The article also disclosed a Table on page 6685 which set forth the inhibition percentage of γ-glutamylcysteine synthetase for each methionine derivative. Of special importance regarding the inhibition of γ-glutamylcysteine synthetase by MSO is its short duration. The inhibition in this case is a matter of hours, as compared to the days of inhibition of glutamine synthetase. Richman, "Inhibition of γ-Glutamylcysteine Synthetase by L-Methionine-S-Sulfoximine," *J. Biological Chemistry* 248:19, 6684–6690 (1973).

The Hawkins reference entitled "Hyperammonaemia Does Not Impair Brain Function in the Absence of Net Glutamine Synthesis" disclosed a series of experiments in which different doses of MSO, ranging from 5 to 200 mg/kg body weight, were injected into the peritoneal cavity of rats. It was noted that the metabolic changes seen in hyperammonaemia, whether caused by injections of urease or portacaval shunting, occurred within the first two days. It was also noted that a single intraperitoneal injection of MSO raises the brain concentration of ammonia within 2 hours. The response to the range of doses was disclosed in FIG. 1 of the Hawkins reference. This data has been reproduced in the attached FIG. 3 as percent inhibition rather than percent normal. It was noted that glutamine synthetase activity was decreased in proportion to the dose and that the decrease in enzyme activity was accompanied by a parallel decrease in the brain content of glutamine. As hypothesized, the plasma ammonia values increased as a function of dose and there was no evidence of toxicity except at the highest dose of 200 mg/kg body weight. It was also disclosed that a smaller dose of MSO, given intravenously, decreased brain glutamine synthetase activity as much as the larger intraperitoneal dose.

Finally, it should be observed that the IV drug administered to the rats in this paper was at a dosage of 30 mg/kg, the toxicity of which to primates is unknown. As seen by the Gershoff reference, the administration of 100 and 50 mg/kg to primates had not adverse effect on the test subject. However, the effect a lower dosage (such as 30 mg/kg) is not disclosed by Gershoff and Hawkins' testing of rats does not aid in this determination. Additionally, while the Hawkins reference does not disclose the MSO isomer used, one of ordinary skill could conclude that the LSMSO isomer was used given the congruity of the Hawkins data and the present invention's data. This reference shows that at LSMSO doses of less than 20 mg/kg in rats results in a dramatic decrease in glutamine synthetase inhibition. Further, it is noted that the IV protocol used in Hawkins used 30 mg/kg of LSMSO (presumably) which is significantly higher than the dosages disclosed in the present invention. Hawkins, "Hyperammonaemia Does Not Impair Brain Function in the Absence of Net Glutamine Synthesis," *Biochem J.* 277:697–703 (1991).

The Takahashi reference entitled "Inhibition of Brain Glutamine Accumulation Prevents Cerebral Edema in Hyperammonemic Rats" disclosed that the inhibition of glutamine synthetase activity by pre-treatment with L-methionine S-sulfoximine prevented both the increase in brain glutamine levels and the increase in brain water content despite elevated plasma ammonium levels. It was determined that cerebral edema during hyperammonemia is associated with glutamine accumulation. It was also disclosed that within the brain, MSO pretreatment produced a 64% inhibition of glutamine synthetase activity, in agreement with others. It was also noted that cortical glutamine levels were increased 3.3-fold in group III hyperammonemic rats compared with group I control rats. In contrast, the cortical glutamine levels did not increase with MSO pretreatment in group IV hyperammoneamic rats. Cortical glutamate levels were slightly decreased only in hyperammonemic rats untreated with MSO. Further, the specific gravity of the cortical tissue was not decreased when the test subjects were pretreated with MSO. Additionally, an increase in brain water was also prevented by the pretreatment of the subjects with MSO. It was concluded that MSO pretreatment resulted in preventing the increase in cortical glutamine and that the effect of MSO in the brain appears to be specific for glutamine synthetase. The data reported in this paper in Table 1 on page H827 is hereby incorporated by reference. Takahashi, "Inhibition of Brain Glutamine Accumulation Prevents Cerebral Edema in Hyperammonemic Rats," *American Physiological Society* 261:H825–H829 (1991).

The Hawkins reference entitled "Effect of Reducing Brain Glutamine Synthesis on Metabolic Symptoms of Hepatic Encephalopathy" disclosed that 24 hours after portacaval shunting, the shunted rats showed characteristic metabolic abnormalities. Treatment with MSO at the time of surgery has no effect on the brain or plasma ammonia concentrations compared with the values in the untreated rats. Brain glutamine content which increased in hyperammonemic MSO untreated animals did not increase in the hyperammonemic MSO treated animals. The article concluded that this indicated that the activity of brain glutamine synthetase had been reduced in the treated rats. The article also concluded that although signs of improvement were seen when presumed glutamine synthetase was inhibited by MSO, this could not be taken as a recommendation for its therapeutic use. Hawkins, "Effect of Reducing Brain Glutamine Synthesis on Metabolic Symptoms of Hepatic Encephalopathy," Journal of Neurochemistry 60:3, 1000–1006 (1993).

The Blei reference entitled "Ammonia-Induced Brain Edema and Intracranial Hypertension in Rats After Portacaval Anastomosis" disclosed that when portacaval anastomosis rats were infused with ammonium acetate and pretreated with 150 mg/kg MSO, brain edema was ameliorated and intracranial pressure did not rise. A dose-dependent reduction in brain glutamine levels was seen with increasing doses of MSO, but brain edema did not decrease beyond the 150 mg/kg dose. The article posited that the increase in brain water was not solely a result of the glutamine accumulation. Blei, "Ammonia-Induced Brain Edema and Intracranial Hypertension in Rats After Portacaval Anastomosis," *Hepatology* 19:6, 1437–1444 (1994).

The Brusilow reference entitled "Urea Cycle Disorders: Diagnosis, Pathophysiology, and Therapy" disclosed that brain glutamine accumulation can be prevented by pretreatment of hyperammonemic rats with MSO, thereby preventing cerebral edema. It was also noted that MSO prevents ammonia-induced swelling of primary astrocyte cultures. Brusilow, "Urea Cycle Disorders: Diagnosis, Pathophysiology, and Therapy," Advances in Pediatrics 43:127–170 (1996).

The Hirata reference entitled "Impaired Pial Arteriolar Reactivity to Hypercapnia During Hyperammonemia Depends on Glutamine Synthesis" disclosed the depressed CBF response to hypercapnia could be prevented by glutamine synthetase inhibition with MSO. It was also determined that MSO can inhibit γ-glutamylcysteine synthetase reversibly. It will not decrease glutathione in the brain, though. It was also demonstrated that MSO inhibited, in this model of acute hyperammonemia, cortical glutamine synthetase by 64%, prevented 13-mmol/kg increase in cortical glutamine concentration, prevented the increase in tissue water content, prevented the increase in cisterna magna pressure, and prevented the loss of the CBF response to hypercapnia. It was also demonstrated that MSO prevents loss of the pial arteriolar dilator response to hypercapnia. Hirata, "Impaired Pial Arteriolar Reactivity to Hypercapnia During Hyperammonemia Depends on Glutamine Synthesis," *Stroke* 27:4, 729–736 (1996).

The Willard-Mack reference entitled "Inhibition of Glutamine Synthetase Reduces Ammonia-Induced Astrocyte Swelling in Rat" disclosed decreases flux through glutamine synthetase and may reduce glutamine flux through glutaminase indirectly by reducing the available glutaminate and by increasing ammonia. It was also shown that the inhibition of glutamine synthetase with MSO attenuates the reduced cytoplasmic electron density, increased water content, increased nuclear circumference, and expansion of small processes in the neuropil and the perivascular endfeet. It also was disclosed that MSO does not prevent enlargement of the perikaryon and its large processes associated with increased numbers of organelles. Finally, the Willard-Mack reference also discussed the role of the MSO inhibitory effect on gamma glutamyl cysteine synthetase by showing that buthionine sulfoximine, which is an inhibitor of gamma glutamyl cysteine synthetase, did not prevent hyperammonemic brain swelling. The data disclosed by this reference on pages 594–596 is incorporated herein by reference. Willard-Mack, "Inhibition of Glutamine Synthetase Reduces Ammonia-Induced Astrocyte Swelling in Rat," *Neuroscience* 71:2, 589–599 (1996).

The Sugimoto reference entitled "Methionine Sulfoximine, A Glutamine Synthetase Inhibitor, Attenuates Increased Extracellular Potassium Activity During Acute Hyperammonemia" disclosed that hyperammonemia causes glutamine accumulation and astrocyte swelling, and that the inhibition of glutamine synthesis would reduce the ammonia-induced edema formation and watery swelling in astrocyte processes. The article concluded that acute hyperammonemia impairs astrocytic control of $[K^+]_e$ and that his impairment is linked to glutamine accumulation rather than ammonium ions per se. Sugimoto, "Methionine Sulfoximine, A Glutamine Synthetase Inhibitor, Attenuates Increased Extracellular Potassium Activity During Acute Hyperammonemia," *Journal of Cerebral Blood Flow & Metabolism* 17:44–49 (1997).

The Master reference entitled "Cerebral Blood Flow and the Development of Ammonia-Induced Brain Edema in Rats After Portacaval Anastomosis" disclosed that MSO ameliorated both the degree of brain edema and the increase in CBF seen in ammonia-infused PCA rats. It also restored the cerebrovascular $CO_2$ responsivity in normal hyperammonemic animals. Master, "Cerebral Blood Flow and the Development of Ammonia-Induced Brain Edema in Rats After Portacaval Anastomosis," *Hepatology* 30:4, 876–880 (1999).

Cerebral edema, brain stem compression and death are the inevitable consequences of uncontrolled clinical hyperammonemia. It is well established that the pathophysiology of hyperammonemic encephalopathy consists of cerebral edema. There is also considerable and increasing evidence to suggest that the cerebral edema consists exclusively of swollen astrocytes. It has been shown that astrocytes swell as a result of hyperammonemia-induced glutamine synthesis, and that the accumulated glutamine serving as an intracellular osmolyte which causes water to shift into the cell.

In 1985, Brusilow offered the hypothesis that cerebral edema associated with hyperammonemia was a consequence of astrocyte brain glutamine accumulation catalyzed by glutamine synthetase, the principal brain sites of which are astrocytes. Accordingly, the inhibition of brain glutamine synthetase should prevent astrocyte glutamine accumulation and thereby prevent astrocyte swelling and cerebral edema in hyperammonemic states. MSO is a well-known and potent inhibitor of glutamine synthetase that possesses inhibitory effects that may persist in the brain for a long as seven days. Lamar at page 638. However, there have been no published dose response studies of L-Methionine S-Sulfoximine's effect on glutamine synthetase in primates.

It has been demonstrated that cerebral edema induced by hyperammonemia can be prevented by inhibiting glutamine synthesis and thereby preventing glutamine accumulation in the astrocytes. The inhibition can be produced by parental administration of L-methionine S-sulfoximine which is a glutamine synthetase inhibitor.

Additional studies have supported the role of glutamine accumulation in producing encephalopathy. This research has uncovered that, among other things, MSO restores cerebral vascular $CO_2$ responsivity in hyperammonemic rats (See Takahashi H, Koehler R C, Hirata T, Brusilow S W. Restoration of Cerebrovascular $CO_2$ Responsivity by Glutamine Synthesis Inhibition in Hyperammonenic Rats. Circ Res 71:1220–1230, 1992), causes inhibition of glutamine synthesis, causes reduced ammonia induced astrocyte swelling in the rat (See Willard-Mack reference), causes inhibition of glutamine synthesis, attenuates increased extracellular potassium activity during acute hyperammonemia (See Sugimoto H, Koehler R C, Wilson D A, Brusilow, Traystman R J. Methionine Sulfoximine, a Glutamine Synthetase Inhibitor, Attenuates Increased Extracellular Potassium Activity during Acute Hyperammonemia. J Cerebr Blood Flow and Metab 17: 44–49, 1997) and causes inhibition of glutamine synthesis corrects impaired pial arteriolar activity to hypercapnia during hyperammonemia (See Hirata T, Kawaguchi T, Brusilow S W, Traystman R J, Koehler R C. Preserved Hypocapnic Pial Arteriolar Constriction During Hyperammonemia by Glutamine Synthetase Inhibition. Am J Physiol 276 (2 of 2): H456–463, 1999.)

Although it has been thought that the convulsant effect of MSO was linked to its GS inhibitory effect, there is persuasive evidence to suggest that the two effects are unrelated and that MSO might be a useful drug. For example, the mean rat brain glutamine level (an indirect measure of GS activity) decreased to the same degree at MSO doses (mg/kg) of 200, 100, and 50; however the rats receiving the two lower doses "did not differ in any way from the control animals" whereas the animals receiving the highest dose had seizures (see Folbergrova, "Free Glutamine Level in the Rat Brain In Vivo After Methionine Sulphoximine Administration," *Physiologia Bohemoslovenica* 13:21–26 (1963)). However, the precise dosages of MSO in these and many other studies are uncertain because the steroisomers administered are not fully described. The Sellinger reference also demonstrated that L-methionine protected rats from the convulsant effect of MSO, but did not affect MSO's inhibition of GS. Additionally, Sellinger disclosed the effect of MSO when administered intraventricularly. The clinical effect of mixed isomers of MSO has been evaluated in two primate studies. Monkeys were found to tolerate doses of mixed MSO isomers in the range of 50 and 100 mg/kg "without observable effect"; GS activity, though, was not measured (see Krakoff). Also, when mixed isomers of MSO were given in daily doses to terminally ill cancer patients, significant side effects such as agitation, disorientation and hallucinations were noted after two days (see Krakoff). Interpretation of this study was hindered by the dire status of the patients and the potential cumulative effect of daily doses, a regimen probably not necessary for an irreversible inhibitor of glutamine synthetase which possess an inhibition duration of at least seven days (see Lamar and Folbergrova references). Because there are species specific responses to MSO, a dose response evaluation of the active isomer, L-methionine S-sulfoximine on GS activity and clinical symptoms in primates may reveal a dose that inhibits GS activity in the absence of an epileptogenic effect and thereby be useful in treating hyperammonemic encephalopathy regardless of etiology.

SUMMARY OF THE INVENTION

Cerebral edema in hyperammonemia is a consequence of hyperammonemia induced intracellular glutamine synthesis. Glutamine serves as an osmolyte, causing water to enter the cell and cause brain swelling (cerebral edema).

It is known that by inhibiting glutamine synthesis with MSO, glutamine does not accumulate during hyperammonemia. As a consequence, glutamine cannot serve as an intracellular organic osmolyte, thereby preventing cerebral edema.

As stated above, one unfortunate side effect of MSO is its known property as a convulsant. In sufficient quantities, this compound has been proven to cause convulsions in human beings, as well as other animals. However, it has now been discovered that LSMSO may be administered in limited amounts while still retaining the ability to prevent and reduce brain swelling. The result of these limited doses are reduced swelling and the lack of the convulsant side effect. The presently claimed dosage of the active LS isomer of MSO yields the requisite inhibition of glutamine synthetase and does not produce adverse neurologic signs, such as seizures. The novel dosage amounts of L-Methionine S-sulfoximine that produces this effect is the subject of this application.

The present invention contemplates a method of treating primates, especially humans, suffering from progressive hyperammonemic encephalopathy. The claimed method comprises the administration of L-methionine S-sulfoximine (hereinafter "LSMSO") in dosages of 10 mg/kg or less which is sufficient to alleviate and reduce the swelling of the brain without the convulsant side-effects produced by MSO.

DETAILED DISCLOSURE

As stated above, one unfortunate and well known side effect of MSO is that it is a convulsant. This property has resulted in its non-use in the treatment of encephalopathy. It has now been discovered that when LSMSO, alone, is administered in low doses, no seizures are produced. It is believed that these lower doses of LSMSO also inhibit the brain glutamine synthetase because the doses lowered brain glutamine levels. In turn, these non-seizure causing doses of LSMSO can be used to treat or prevent cerebral edema in subjects with hyperammonemic states.

The claimed invention comprises treating subjects in the various stages of progressive hyperammonemic encephalopathy with low doses of LSMSO of no more than 10 mg/kg, preferably no more than 8 mg/kg, more preferably no more than 5 mg/kg, and most preferably no more than 2.5 mg/kg. The LSMSO can be administered to subjects, for example, patients with symptomatic chronic low grade hyperammonemia, subjects with increasing plasma ammonium levels, and also subjects with high risk of developing hyperammonemia. It is believed that this treatment prevents any further brain glutamine accumulation and, therefore, prevents any further increase in cerebral edema. The results obtained in the treatment of progressive hyperammonemic encephalopathy reported herein suggests that LSMSO may also be administered in the amounts specified herein to patients suffering from other diseases in which the inhibition of glutamine synthetase would be beneficial. However, the present invention is not intended for use in patients with far-advanced, nonresectable cancers.

The claimed invention also results in reduced brain swelling, minimizes or prevents seizures, the inhibition of glutamine synthetase, and the minimization or prevention of neurologic symptoms.

The LSMSO may be administered to the subject orally, intravenously, or subcutaneously. The IV preparation can be administered as a sterile buffered saline solution, while the oral preparation will be prepared with the standard pharmaceutically acceptable excipients through standard pharmaceutical manufacturing techniques.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, and cachets.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water or other appropriate solvents and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active LSMSO. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

As pharmaceutical compositions for treating cerebral edema, the compounds of the present invention are generally in a pharmaceutical composition so as to be administered to a subject at dosage levels of no more than 10.0 mg/kg per day, and preferably no more than 8.0 mg/kg per day, and more preferably no more than 5.0 mg/kg per day, and most preferably at no more than 2.5 mg/kg per day for a normal human adult of approximately 70 kg of body weight. For such a normal human adult, these amounts correspond to a dose of 700 mg, 560 mg, 350 mg, and 175 mg, respectively. The specific dosages employed, however, can be varied depending upon the requirements of the patient, and the severity of the condition being treated. The determination of optimum dosages for a particular situation is within the skill of the art.

BRIEF DESCRIPTION OF DRAWINGS

FIG. 1 presents a species difference in the inhibitory effect of LSMSO on primates as compared to rats and a comparison of the effect of low dose intravenous L-methionine S-sulfoximine (LSMSO) on the inhibition of glutamine synthetase was studied in rat brain and Rhesus monkey brain and compared to the Hawkins (1991) data. The Hawkins data is represented with closed circles whereas the comparison tested rats are represented with "+" and open circle symbols. The monkey results are shown with triangles. N represents the number of animals studied.

EXAMPLES

Example 1

Figure 1:
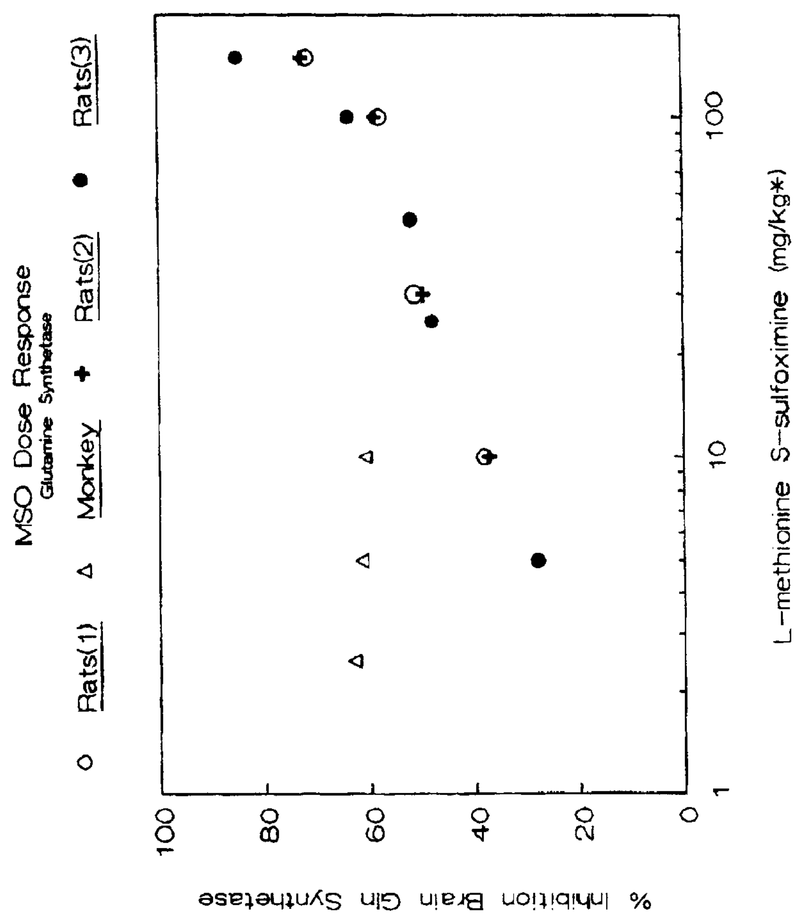
FIG. 1.

The effect of low dose intravenous L-methionine S-sulfoximine (LSMSO) on the inhibition of glutamine synthetase was studied in rat brain and Rhesus monkey brain and compared to the Hawkins (1991) data. Apart from a brief anesthesia to permit the injection of the drug, the rats were awake and asymptomatic for 24 hours prior to sacrifice. The monkeys who received LSMSO at doses of 5 and 10 mg/kg were anesthetized for a four hour period prior to sacrifice. One monkey received a 2.5 mg/kg dose of MSO had a brief anesthesia to permit the injection of the drug, but was awake for 24 hours prior to sacrifice. This monkey's activity and appetite were normal during the 24 hour period prior to sacrifice. The results of the study are illustrated in FIG. 1. However, it is apparent from the results reflected in FIG. 1 that primates are more sensitive to the glutamine synthetase inhibiting effect of MSO at low doses, which can be an advantageous effect allowing the minimization or prevention of the epileptogenic effect of MSO.

References Cited

Blei, "Ammonia-induced Brain Edema and Intracranial Hypertension in Rats After Portacaval Anastomosis," *Hepatology* 19:6,1437–1444 (1994).

Brusilow, "Urea Cycle Disorders: Diagnosis, Pathophysiology, and Therapy," Advances in Pediatrics 43:127–170 (1996).

Butterworth, "Effects of Hyperammonaemia on Brain Function," *J. Inher. Metab. Dis*. 21 (suppl 1):6–20 (1998).

Folbergrova, "Free Glutamine Level in the Rat Brain In Vivo After Methionine Sulphoximine Administration," *Physiologia Bohemoslovenica* 13:21–26 (1963).

Hawkins, "Effect of Reducing Brain Glutamine Synthesis on Metabolic Symptoms of Hepatic Encephalopathy," Journal of Neurochemistry 60:3, 1000–1006 (1993).

Hawkins, "Hyperammonaemia Does Not Impair Brain Function in the Absence of Net Glutamine Synthesis," *Biochem J*. 277:697–703 (1991).

Hirata, "Impaired Pial Arteriolar Reactivity to Hypercapnia During Hyperammonemia Depends on Glutamine Synthesis," *Stroke* 27:4, 729–736 (1996).

Jonung, "Methionine Sulfoximine Prevents the Accumulation of Large Neutral Amino Acids in Brain of Hyperammonemic Rats," *J. Surgical Research* 36:349–353 (1984).

Krakoff, Effect of Methionine Sulfoximine in Man," *J. Pharm. Experimental Ther*., 2:599–604 (1961).

Lamar, "The Duration of the Inhibition of Glutamine Synthetase by Methionine Sulfoximine," *Biochemical Pharmacology* 17: 636–642 (1968).

Master, "Cerebral Blood Flow and the Development of Ammonia-Induced Brain Edema in Rats After Portacaval Anastomosis," *Hepatology* 30:4, 876–880 (1999).

Rowe, "Identification of L-Methionine-S-Sulfoximine as the Convulsant Isomer of Methionine Sulfoximine," *Proceedings of the National Academy of Sciences* 66:2, 500–506 (1970).

Richman, "Inhibition of γ-Glutamylcysteine Synthetase by L-Methionine-S-Sulfoximine," *J. Biological Chemistry* 248:19, 6684–6690 (1973). Sellinger, "Methionine Sulfoximine Seizures. VII. The Dissociation of the Convulsant and Glutamine Synthetase Inhibitory Effects," *J. Pharmacology & Experimental Therapeutics* 161:1, 212–222 (1968).

Sugimoto, "Methionine Sulfoximine, A Glutamine Synthetase Inhibitor, Attenuates Increased Extracellular Potassium Activity During Acute Hyperammonemia," *Journal of Cerebral Blood Flow & Metabolism* 17:44–49 (1997).

Takahashi, "Inhibition of Brain Glutamine Accumulation Prevents Cerebral Edema in Hyperammonemic Rats," *American Physiological Society* 261:H825–H829 (1991).

Wada, "The Susceptibility to Auditory Stimuli of Animals Treated with Methionine Sulfoximine," *Experimental Neurology* 15:157–163 (1966).

Warren, "Effect of an Inhibitor of Glutamine Synthesis (Methionine Sulfoximine) on Ammonia Toxicity and Metabolism," *J. Lab. & Clin. Med.* 64:3, 442449 (1964).

Willard-Mack, "Inhibition of Glutamine Synthetase Reduces Ammonia-Induced Astrocyte Swelling in Rat," *Neuroscience* 71:2, 589–599 (1996).

Zwingmann C, Brand A, Richter-Landsberg C, Leibfritz D. Multinuclear NMR spectroscopy studies on $NH_4Cl$-induced metabolic alterations and detoxification processes in primary astrocytes and glioma cells. Developmental Neuroscience 20:417–426 1998.

What is claimed is:

1. A method of treating progressive hyperammonemic encephalopathy in primates comprising administering L-methionine S-sulfoximine to a primate in need of such treatment in an amount effective to reduce swelling and minimize or inhibit seizures, wherein the amount is no more than 10.0 mg/kg.

2. The method of claim 1, wherein the primate is a human.

3. The method of claim 2, wherein the subject in need of such treatment suffers from brain swelling.

4. The method of claim 2, wherein the amount of L-methionine S-sulfoximine is the maximum amount administered over a one week period.

5. The method of claim 4, wherein the amount of L-methionine S-sulfoximine is no more than 8.0 mg/kg.

6. The method of claim 4, wherein the amount of L-methionine S-sulfoximine is no more than 5 mg/kg.

7. The method of claim 4, wherein the amount of L-methionine S-sulfoximine is no more than 2.5 mg/kg.

8. A method of treating progressive hyperammonemic encephalopathy in a primate subject comprising administering to a subject with symptomatic chronic low grade hyperammonemia a dose of L-methionine S-sulfoximine in an amount effective to inhibit glutamine synthetase and minimize or inhibit neurologic symptoms, said amount being no more than 10.0 mg/kg.

9. The method of claim 8, wherein the primate subject is a human.

10. The method of claim 9, wherein the amount of L-methionine S-sulfoximine is the maximum amount administered over a one week period.

11. The method of claim 10, wherein the amount of L-methionine S-sulfoximine is no more than 5 mg/kg.

12. The method of claim 10, wherein the amount of L-methionine S-sulfoximine is no more than 2.5 mg/kg.

13. The method of claim 9, wherein the amount of L-methionine S-sulfoximine is no more than 8.0 mg/kg.

14. A method of treating progressive hyperammonemic encephalopathy in a primate subject comprising administering to the subject with increasing plasma ammonium levels a dose of L-methionine S-sulfoximine in an amount effective to inhibit glutamine synthetase and minimize or inhibit neurologic symptoms, said amount being no more than 10.0 mg/kg.

15. The method of claim 14, wherein the primate subject is a human.

16. The method of claim 15, wherein the amount of L-methionine S-sulfoximine is the maximum amount administered over a one week period.

17. The method of claim 15, wherein the amount of L-methionine S-sulfoximine is no more than 8.0 mg/kg.

18. The method of claim 17, wherein the amount of L-methionine S-sulfoximine is no more than 5.0 mg/kg.

19. The method of claim 17, wherein the amount of L-methionine S-sulfoximine is no more than 2.5 mg/kg.

20. A method of inhibiting progressive hyperammonemic encephalopathy in a primate subject comprising administering to a subject with high risk of developing hyperammonemia a dose of L-methionine S-sulfoximine in an amount effective to inhibit glutamine synthetase and minimize or inhibit neurologic symptoms, wherein said amount is no more than 10.0 mg/kg.

21. The method of claim 20, wherein the primate subject is a human.

22. The method of claim 21, wherein the amount of L-methionine S-sulfoximine is the maximum amount administered over a one week period.

23. The method of claim 21, wherein the amount of L-methionine S-sulfoximine is no more than 8.0 mg/kg.

24. The method of claim 23, wherein the amount of L-methionine S-sulfoximine is no more than 5.0 mg/kg.

25. The method of claim 23, wherein the amount of L-methionine S-sulfoximine is no more than 2.5 mg/kg.

26. A method of treating a disease susceptible to the inhibition of mammalian glutamine synthetase comprising administering to a primate subject in need of such treatment a pharmaceutically effective amount of L-methionine S-sulfoximine, wherein the pharmaceutically effective amount of L-methionine S-sulfoximine does not exceed 10 mg/kg over a one week period.

27. The method of claim 26, wherein the pharmaceutically effective amount of L-methionine S-sulfoximine does not exceed 8 mg/kg over a one week period.

28. The method of claim 26, wherein the pharmaceutically effective amount of L-methionine S-sulfoximine does not exceed 5 mg/kg over a one week period.

29. The method of 26, wherein the pharmaceutically effective amount of L-methionine S-sulfoximine does not exceed 2.5 mg/kg over a one week period.

30. A method for the treatment of progressive hyperammonemic encephalopathy in an adult human suffering from brain swelling comprising administering to said human L-methionine S-sulfoximine, with the proviso that said L-methionine S-sulfoximine is administered in an amount of no more than 700 mg.

31. The method of claim 30 wherein said L-methionine S-Sulfoximine is administered in an amount of no more than 560 mg.

32. The method of claim 30 wherein said L-methionine S-sulfoximine is administered in an amount of no more than 350 mg.

33. The method of claim 30 wherein said L-methionine S-sulfoximine is administered in an amount of no more than 175 mg.

* * * * *